(12) United States Patent
McConnell et al.

(10) Patent No.: US 11,541,069 B2
(45) Date of Patent: Jan. 3, 2023

(54) ONE OR MORE HMOS FOR REDUCING OR PREVENTING FATIGUE AND/OR IMPROVING FOCUS OR CONCENTRATION

(71) Applicant: Glycom A/S, Hørsholm (DK)

(72) Inventors: Bruce McConnell, La Tour de Peilz (CH); Louise Kristine Vigsnæs, Copenhagen (DK); Ingvild Dybdrodt Amundsen, Copenhagen (DK)

(73) Assignee: Glycom A/S, Hørsholm (DK)

( * ) Notice: Subject to any disclaimer, the term of this patent is extended or adjusted under 35 U.S.C. 154(b) by 13 days.

(21) Appl. No.: 16/761,164

(22) PCT Filed: Nov. 2, 2018

(86) PCT No.: PCT/IB2018/058611
§ 371 (c)(1),
(2) Date: May 1, 2020

(87) PCT Pub. No.: WO2019/087140
PCT Pub. Date: May 9, 2019

(65) Prior Publication Data
US 2020/0338100 A1 Oct. 29, 2020

(30) Foreign Application Priority Data

Nov. 2, 2017 (DK) .............................. PA201700616
Nov. 30, 2017 (DK) .............................. PA201700679
Jun. 25, 2018 (DK) .............................. PA201800293
Aug. 21, 2018 (WO) .................. PCT/IB2018/056308

(51) Int. Cl.
*A61K 31/702* (2006.01)
*A23L 33/125* (2016.01)

(52) U.S. Cl.
CPC .......... *A61K 31/702* (2013.01); *A23L 33/125* (2016.08)

(58) Field of Classification Search
None
See application file for complete search history.

(56) References Cited

U.S. PATENT DOCUMENTS

| | | | |
|---|---|---|---|
| 2015/0305384 A1 | 10/2015 | Chichlowski et al. | |
| 2016/0120915 A1* | 5/2016 | Blaser | A61K 31/7004 424/93.4 |
| 2016/0243139 A1* | 8/2016 | Vigsnæs | A61K 31/7004 |
| 2016/0287637 A1* | 10/2016 | McConnell | A61K 35/20 |
| 2016/0310514 A1* | 10/2016 | Salomonsson | A61K 31/7004 |

FOREIGN PATENT DOCUMENTS

| | | | |
|---|---|---|---|
| EP | 2880993 A1 | 6/2015 | |
| EP | 2888950 A1 * | 7/2015 | ........... A23L 33/125 |
| WO | 01/04341 A1 | 1/2001 | |
| WO | 2007101862 A1 | 9/2007 | |
| WO | 2010115934 A1 | 10/2010 | |
| WO | 2010115935 A1 | 10/2010 | |
| WO | 2011100979 A1 | 8/2011 | |
| WO | 2011100980 A1 | 8/2011 | |
| WO | 2012007588 A9 | 1/2012 | |
| WO | 2012113404 A1 | 8/2012 | |
| WO | 2012113405 A1 | 8/2012 | |
| WO | 2012127410 A1 | 9/2012 | |
| WO | 2012155916 A1 | 11/2012 | |
| WO | 2012156897 A1 | 11/2012 | |
| WO | 2012156898 A1 | 11/2012 | |
| WO | 2013044928 A1 | 4/2013 | |
| WO | 2013091660 A1 | 6/2013 | |
| WO | 2013139344 A1 | 9/2013 | |
| WO | 2014100022 A1 | 6/2014 | |
| WO | 2016086151 A1 | 6/2016 | |
| WO | 2016086157 A1 | 6/2016 | |
| WO | 2017071715 A1 | 5/2017 | |
| WO | 2019038668 A1 | 2/2019 | |

OTHER PUBLICATIONS

Chung, Y. C., Jin, H. M., Cui, Y., Jung, J. M., Park, J. I., Jung, E. S., . . . & Chae, S. W. (2014). Fermented milk of Lactobacillus helveticus IDCC3801 improves cognitive functioning during cognitive fatigue tests in healthy older adults. Journal of functional foods, 10, 465-474. (Year: 2014).*
Jordá, F. C., & Vivancos, J. L. (2010). Fatigue as a determinant of health in patients with celiac disease. Journal of clinical gastroenterology, 44(6), 423-427. (Year: 2010).*
PCT/IB2018/058611, "International Search Report", dated Jan. 9, 2019, pp. 1-8.
PCT/IB2018/058611, "Written Opinion of the International Searching Authority", dated Jan. 9, 2019, pp. 1-4.
Vazquez E. et al.,"Dietary 2'-Fucosyllactose Enhances Operant Conditioning and Long-Term Potentiation via Gu-Brain Communication through the Vagus Nerve in Rodents", Plos One vol. 11, No. 11, Nov. 16, 2016, pp. 1-10.
Wang B. "Molecular Mechanism Underlying Sialic Acid as an Essential Nutrient for Brain Development and Cognition", American Society for Nutrition Adv. Nutrition, vol. 3, No. 3, 2012, pp. 465S-472S.
Oliveros E. et al., "Oral supplementation of 2-fucosyllactose during lactation improves memory and learning in rats", Journal of Nutritional Biochemistry vol. 31, 2016, pp. 20-27.

(Continued)

*Primary Examiner* — Dale R Miller
(74) *Attorney, Agent, or Firm* — Kunzler Bean & Adamson; Tom Briscoe

(57) ABSTRACT

The invention relates to a human milk oligosaccharide (HMO) for use in reducing or preventing fatigue and/or improving focus or concentration on a mental or physical activity in a human. The invention also relates to a synthetic composition for use, comprising one or more of said HMOs. The invention further relates to a method for reducing or preventing fatigue and/or improving focus or concentration on a mental or physical activity by administering at least one HMO and the use of said one or more HMOs in a dietary management of a human.

4 Claims, No Drawings

(56) References Cited

OTHER PUBLICATIONS

F. Bottacini et al., "Diversity, ecology and intestinal function of bifidobacteria", 11th International Symposium on Lactic Acid Bacteria Egmond aan Zee, Microbial Cell Factories 2014, 13(Suppl 1):S4, Aug. 31-Sep. 4, 2014, pp. 1-15.
European Commission, Information from European Union Institutions, Bodies, Offices and Agencies, Official Journal of the European Union C 401/1, Nov. 25, 2017, pp. 1-15.
S. Duranti et al., "Exploration of the Genomic Diversity and Core Genome of the Bifidobacterium adolescentis Phylogenetic Group by Means of a Polyphasic Approach", Applied and Environmental Microbiology, Jan. 2013 Volume 79 Number 1, p. 336-346.
M. Fremont et al., "High-throughput 16S rRNA gene sequencing reveals alterations of intestinal microbiota in myalgic encephalomyelitis/chronic fatigue syndrome patients", SciVerse ScienceDirect, Jun. 19, 2013, pp. 50-56.
Xi Chen, Human Milk Oligosaccharides (HMOS): Structure, Function, and Enzyme-Catalyzed Synthesis, Advances in Carbohydrate Chemistry and Biochemistry, vol. 72 ISSN 0065-2318, 2015, pp. 1-78.
L. Bode, "Human milk oligosaccharides and their beneficial effects", Handbook of dietary and nutritional aspects of human breast milk Human Health Handbooks No. 5 DOI 10.3920/978 90 8686-764-6 30, 2013, pp. 515-531.
Tadasu Urashima et al., Milk Oligosaccharides, Copyright ©2011 by Nova Science Publishers, Inc., 2011, pp. 1-99.

\* cited by examiner

ONE OR MORE HMOS FOR REDUCING OR PREVENTING FATIGUE AND/OR IMPROVING FOCUS OR CONCENTRATION

FIELD OF THE INVENTION

This invention relates to a method, compounds and composition for reduction of fatigue in a human and/or improving focus or concentration on a mental or physical activity.

BACKGROUND OF THE INVENTION

Fatigue is a subjective feeling of tiredness that can have many possible causes and accompanies many different conditions. Fatigue is considered a symptom because it is a subjective feeling reported by the patient, rather than an objective one that can be observed by others. Fatigue is different from sleepiness and is generally considered a more long-term condition than sleepiness.

Generally, fatigue is defined as physical or mental fatigue. Physical fatigue is the transient inability of muscle to maintain optimal physical performance. The onset of muscle fatigue during physical activity is gradual, and depends upon an individual's level of physical fitness, and upon other factors, such as sleep deprivation and overall health. It can usually be reversed by rest. The central component of physical fatigue which is not associated with a specific disease appears to be triggered by an increase of the level of serotonin in the central nervous system. During motor activity, serotonin released in the synapses that contact motoneurons to promote muscle contraction. When the level of motor activity is high, the amount of serotonin released increases and spill over occurs. The serotonin then binds to extra synaptic receptors located on the axon initial segment of motoneurons with the result that nerve impulse initiation and thereby muscle contraction are inhibited. However, the mechanism in certain patient populations may be different.

Mental fatigue is a transient decrease in optimal cognitive performance usually resulting from prolonged periods of cognitive activity; but it may have other causes. It can manifest as somnolence, lethargy, or directed attention fatigue. The onset of mental fatigue is gradual and depends upon an individual's cognitive ability, and upon other factors, such as sleep deprivation and overall health.

Fatigue is usually caused by factors such as working, mental stress, overstimulation, under stimulation, jet lag, depression, boredom, disease and lack of sleep. It may also have chemical causes, such as poisoning, or nutritional causes such as mineral or vitamin deficiencies. Chronic blood loss frequently results in fatigue, as do other conditions that cause anaemia.

Temporary fatigue is a minor condition which is usually addressed through rest. However, many people suffer from prolonged fatigue where rest does not provide relief. Prolonged fatigue is a persistent state of fatigue lasting for a period of time such as at least one month. Prolonged or chronic fatigue is a symptom of many diseases and conditions. Some of the diseases or conditions that include prolonged fatigue as a co-morbidity include: autoimmune diseases such as celiac disease, multiple sclerosis, and Sjogren's syndrome; blood disorders such as anaemia and hemochromatosis; cancer; chronic fatigue syndrome; depression and other mental disorders that feature depressed mood; endocrine diseases like diabetes mellitus; irritable bowel syndrome; sleep deprivation or sleep disorders; and allergies and food intolerances.

One example of prolonged fatigue is Chronic Fatigue Syndrome (CFS), a multisystem illness, associated with disabling fatigue, cognitive dysfunction and sleeping disturbances. In 1992, the WHO approved the term "Chronic Fatigue Syndrome" and recognized this disorder as a neurological disease (WHOICD-10G93.3). CFS is characterized by persistent and relapsing fatigue, post exertional malaise (both physical and mental), cognitive and mood changes, and gastrointestinal disturbance and food intolerances. In addition, sleep disturbances and unrefreshing sleep are commonly reported by these patients. While there are now internationally recognized criteria for diagnosing this disorder, the cause (or causes) is unknown. However, it has recently been proposed that CFS is associated with imbalances in intestinal microbiota (dysbiosis) (Fremont et al. *Anaerobe* 22, 50 (2013)). Several other conditions such as celiac disease, depression, diabetes mellitus, irritable bowel syndrome, allergies and food intolerances are also associated with imbalances in intestinal microbiota. In all of these diseases and conditions, there is no adequate treatment for the fatigue symptoms of the condition. One of the main consequence of fatigue is lack of focus or concentration on mental or physical activities.

Therefore, there remains a need for methods and compounds for addressing fatigue in humans. Further, there remains a need for methods and compounds for improving focus or concentration on a mental or physical activity.

SUMMARY OF THE INVENTION

A first aspect of the invention relates to a human milk oligosaccharide (HMO) for use in reducing fatigue and/or improving focus or concentration on a mental or physical activity in a human.

A second aspect of the invention relates to a synthetic composition for use in reducing fatigue and/or improving focus or concentration on a mental or physical activity in a human, the composition comprising at least one human milk oligosaccharide (HMO).

Preferably, the synthetic composition contains an amount of 1 g to 15 g of the HMO; more preferably 2 g to 10 g. For example, the synthetic composition may contain 3 g to 7 g of the HMO.

A third aspect of the invention relates to a method for reducing fatigue and/or improving focus or concentration on a mental or physical activity in a human, the method comprising administering to the human an effective amount of at least one human milk oligosaccharide (HMO).

A fourth aspect of the invention is a use of
- one or more human milk oligosaccharides (HMOs), or
- a synthetic composition comprising one or more human milk oligosaccharides (HMOs),in the dietary management of a human in need of reducing fatigue and/or improving focus or concentration on a mental or physical activity.

Preferably, the human is administered an amount of 1 g to 15 g per day of the HMO; more preferably 2 g to 10 g per day. For example, the human may be administered 3 g to 7 g per day. Preferably the human is administered the HMO for a period of at least 1 week; more preferably for at least 2 weeks or longer, such as e.g. 3-4 weeks, 1-2 months.

During an initial treatment phase, the human may be administered a higher amount of the HMO, for example 3 g to 15 g per day, preferably 3 g to 10 g per day. During a subsequent maintenance phase, the human may be administered a lower amount of the HMO, for example, 1 g to 10 g per day, preferably 2 g to 7.5 g per day. Preferably, the initial treatment phase has a duration of at least 3 weeks, preferably about 1 month or longer, preferably up to about 2 months, such as about 6, 7, 8 or 9 weeks. The duration of the maintenance phase could be at least about 1 month, preferably longer, such as at least about 6 to 8 weeks, or about 10-12 weeks. The term "about" in the present context means +/−1-3 days.

The human can suffer from a disease or condition that includes prolonged fatigue as a co-morbidity. For example, the disease or condition is an autoimmune disease (such as celiac disease, multiple sclerosis, and Sjogren's syndrome), a blood disorder (such as anaemia and hemochromatosis), a cancer, chronic fatigue syndrome, depression or another mental disorder that feature depressed mood, an endocrine disease (such as diabetes mellitus), irritable bowel syndrome, sleep deprivation or a sleep disorder, an allergy and/or a food intolerance. Preferably the human is a non-infant human.

The HMO can be a neutral HMO or an acidic HMO. The neutral HMO can be one or more fucosylated HMOs or one or more non-fucosylated HMOs. Preferably, the HMO is selected from 2'-FL, 3-FL, DFL, LNT, LNnT, 3'-SL, 6'-SL, LNFP-I or a mixture thereof. Preferably, the HMO comprises or consists of 2'-FL and (LNnT and/or LNT); 2'-FL, DFL and (LNnT and/or LNT); 2'-FL and 6'-SL; 2'-FL, DFL and 6'-SL; 2'-FL, 6'-SL and (LNnT and/or LNT); and 2'-FL, DFL, 6'-SL and (LNnT and/or LNT).

DETAILED DESCRIPTION OF THE INVENTION

Human milk oligosaccharides (HMOs) are a heterogeneous mixture of soluble glycans found in human milk. They are the third most abundant solid component after lactose and lipids in human milk and are present in concentrations of 5-25 g/l (Bode: *Human milk oligosaccharides and their beneficial effects*, in: Handbook of dietary and nutritional aspects of human breast milk (Zibadi et al., eds.), pp. 515-3, Wageningen Academic Publishers (2013)). HMOs are resistant to enzymatic hydrolysis in the small intestine and are thus largely undigested and unabsorbed and reach the colon intact. The majority of HMOs that reach the colon serve as substrates to shape the gut ecosystem by selectively stimulating the growth of specific bacteria. HMOs are believed to substantially modulate the infant gut microbiota and play a decisive role in the differences in the microbiota of formula-fed and breast-fed infants. These differences include the predominance of *Bifidobacterium* in the gut of breast-fed infants compared to a more diverse gut microbiota in formula-fed infants. This is viewed as beneficial for the infant because strains of *Bifidobacterium* species are believed to have a positive effect on gut health.

It has now been surprisingly found that HMOs, when administered to humans, are able to reduce fatigue and/or improve focus or concentration on a mental or physical activity in the human; including humans suffering from diseases or medical conditions. The HMOs also preferentially increase the abundance of bifidobacteria in the gastro-intestinal tract, in particular bifidobacteria of the *B. adolescentis* phylogenetic group, *Bifidobacterium longum* and/or *Bifidobacterium bifidum*. Further, administration of HMOs results in improvement, enhancement, promotion or modulation a GABAergic function in the CNS which may contribute to the reduction in fatigue and/or improvement focus or concentration on a mental or physical activity.

In this specification, the following terms have the following meanings:

"Non-infant human" or "non-infant" means a human of 3 years of age and older. A non-infant human can be a child, a teenager, an adult or an elderly.

"Human milk oligosaccharide" or "HMO" means a complex carbohydrate found in human breast milk (Urashima et al.: Milk Oligosaccharides. Nova Science Publisher (2011); Chen *Adv. Carbohydr. Chem. Biochem.* 72, 113 (2015)). The HMOs have a core structure comprising a lactose unit at the reducing end that can be elongated by one or more β-N-acetyl-lactosaminyl and/or one or β-more lacto-N-biosyl units, and which core structure can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH) .Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose 11 (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

"Synthetic composition" means a composition which is artificially prepared and preferably means a composition containing at least one compound that is produced ex vivo chemically and/or biologically, e.g. by means of chemical reaction, enzymatic reaction or recombinantly. In some embodiments a synthetic composition of the invention may be, but preferably is not, identical with a naturally occurring composition. The synthetic composition typically comprises one or more compounds, including one or more HMOs, that are capable of reducing fatigue in a human. Also, in some embodiments, the synthetic compositions may comprise one or more nutritionally or pharmaceutically active components which do not affect adversely the efficacy of the above-mentioned compounds. Some non-limiting embodiments of a synthetic composition of the invention are also described below.

"Microbiota", "microflora" and "microbiome" mean a community of living microorganisms that typically inhabits a bodily organ or part, particularly the gastro-intestinal organs of humans. The most dominant members of the gastrointestinal microbiota include microorganisms of the phyla of *Firmicutes, Bacteroidetes, Actinobacteria, Proteobacteria, Synergistetes, Verrucomicrobia, Fusobacteria*, and *Euryarchaeota*; at genus level *Bacteroides, Faecalibacterium, Bifidobacterium, Roseburia, Alistipes, Collinsella, Blautia, Coprococcus, Ruminococcus, Eubacterium* and *Dorea*; at species level *Bacteroides uniformis, Alistipes*

*putredinis, Parabacteroides merdae, Ruminococcus bromii, Dorea longicatena, Bacteroides caccae, Bacteroides thetaiotaomicron, Eubacterium hallii, Ruminococcus torques, Faecalibacterium prausnitzii, Ruminococcus lactaris, Collinsella aerofaciens, Dorea formicigenerans, Bacteroides vulgatus* and *Roseburia intestinalis*. The gastrointestinal microbiota includes the mucosa-associated microbiota, which is located in or attached to the mucus layer covering the epithelium of the gastrointestinal tract, and luminal-associated microbiota, which is found in the lumen of the gastrointestinal tract.

"Enteral administration" means any conventional form for delivery of a composition to a non-infant that causes the deposition of the composition in the gastrointestinal tract (including the stomach). Methods of enteral administration include feeding through a naso-gastric tube or jejunum tube, oral, sublingual and rectal.

"Oral administration" means any conventional form for the delivery of a composition to a non-infant through the mouth. Accordingly, oral administration is a form of enteral administration.

"Effective amount" means an amount of a composition that provides an HMO in a sufficient amount to render a desired treatment outcome in a human. An effective amount can be administered in one or more doses to achieve the desired treatment outcome.

"Relative abundance of a bifidobacteria" means the abundance of a bifidobacteria species relative to other bifidobacteria in the microbiota of the gastro-intestinal tract of humans.

"Relative growth of a bifidobacteria" means the growth of a bifidobacteria species relative to other bifidobacteria in the microbiota in the gastro-intestinal tract of humans.

"*Bifidobacterium* of the *B. adolescentis* phylogenetic group" means a bacterium selected from a group consisting of *Bifidobacterium adolescentis, Bifidobacterium angulatum, Bifidobacterium catenulatum, Bifidobacterium pseudocatenulatum, Bifidobacterium kashiwanohense, Bifidobacterium dentum* and *Bifidobacterium stercoris* (Duranti et al. *Appl. Environ. Microbiol.* 79, 336 (2013), Bottacini et al. *Microbial Cell Fact.* 13:S4 (2014)). Preferably, a *Bifidobacterium* of the *B. adolescentis* phylogenetic group is *Bifidobacterium adolescentis* and/or *Bifidobacterium pseudocatenulatum*.

"Treat" means to address a medical condition or disease with the objective of improving or stabilising an outcome in the person being treated. Treat includes the dietary or nutritional management of the medical condition or disease by addressing nutritional needs of the person being treated. "Treating" and "treatment" have grammatically corresponding meanings.

"Modulating of microbiota" means exerting a modifying or controlling influence on microbiota, in particular an influence leading to an increase in the indigenous intestinal abundance of *Bifidobacterium, Bamesiella* and/or butyrate-producing bacteria such as *Faecalibacterium*, and reduction of the intestinal abundance of *Ruminococcus gnavus* and/or Proteobacteria. "Proteobacteria" are a phylum of Gram-negative bacteria and include a wide variety of pathogenic bacteria, such as *Escherichia, Salmonella, Vibrio, Helicobacter, Yersinia* and many other notable genera.

"Therapy" means treatment given or action taken to reduce or eliminate symptoms of a disease or pathological condition.

"Preventive treatment" or "prevention" in the present context means treatment given or action taken to diminish the risk of onset or recurrence of a disease. In accordance with this invention, fatigue in a human, both as primary condition or co-morbidity to a disease or a pathological condition, e.g. an autoimmune disease (such as celiac disease, multiple sclerosis, and Sjögren's syndrome), a blood disorder (such as anaemia and hemochromatosis), a cancer, chronic fatigue syndrome, depression or another mental disorder that feature depressed mood, an endocrine disease (such as diabetes mellitus), irritable bowel syndrome, sleep deprivation or a sleep disorder, an allergy and/or a food intolerance, may be reduced or prevented by administering one or more HMOs to the human. The prevention can occur by addressing underlying nutritional needs of the human or through other mechanisms. The HMOs may be administered as individual compounds or in the form of a synthetic composition.

"Dietary management" means exclusive or partial feeding of patients who, because of a disease, disorder or medical condition are suffering from:

either have a limited, impaired or disturbed capacity to take, digest, absorb, metabolise or excrete ordinary food or certain nutrients contained therein, or metabolites, or have other medically-determined nutrient requirements (see: Commission Notice on the classification of Food for Special Medical Purposes of the European Commission, *Official Journal of the European Union* C 401, 25.11.2017, p. 10-11).

The HMO can be a neutral HMO or an acidic HMO, or a mixture of both. The neutral HMO is, in one embodiment, one or more fucosylated HMOs; in another embodiment, the HMO is one or more non-fucosylated HMOs. In one embodiment, the neutral HMO is a mixture of neutral HMOs, preferably a mixture comprising or consisting of a fucosylated and a non-fucosylated neutral HMO. Particularly, the mixture contains, consists or consists essentially of one or more fucosylated neutral HMO selected from the list consisting of 2'-FL, 3-FL, DFL, LNFP-I, LNFP-II, LNFP-III, LNFP-V, LNFP-VI, LNDFH-I, LNDFH-II, LNDFH-III, FLNH-I, FLNH-II, FLNnH, FpLNH-I and F-pLNnH II, preferably, at least 2'-FL, and a non-fucosylated neutral HMO selected from the list consisting of LNT, LNnT, LNH, LNnH, pLNH and pLNnH, e.g. LNnT. In some preferred embodiment, the mixture contains, consists or consists essentially of a fucosylated neutral HMO selected from the list consisting of 2'-FL, 3-FL and DFL, and a non-fucosylated neutral HMO selected from the list consisting of LNT and LNnT, advantageously the mixture comprises, consists or consists essentially of i) 2'-FL and/or DFL and ii) LNnT and/or LNT (meaning that the mixture comprises, consists or consists essentially of at least one of 2'-FL and DFL, and at least one of LNnT and LNT, for example a mixture comprising, consisting or consisting essentially of 2'-FL and LNnT; or 2'-FL, DFL and LNnT). The mixture can also be that containing, consisting or consisting essentially of 2'-FL and DFL. In another embodiments, the acidic HMOs are preferably selected from 3'-SL and 6'-SL. Exemplary HMO mixtures containing an acidic HMO are those comprising, consisting or consisting essentially of 2'-FL and 6'-SL; 2'-FL, DFL and 6'-SL, 2'-FL, 6'-SL and LNnT; or 2'-FL, DFL, 6'-SL and LNnT.

The HMOs can be isolated or enriched by well-known processes from milk(s) secreted by mammals including, but not limited to human, bovine, ovine, porcine, or caprine species. The HMOs can also be produced by well-known processes using microbial fermentation, enzymatic processes, chemical synthesis, or combinations of these technologies. As examples, using chemistry LNnT can be made as described in WO 2011/100980 and WO 2013/044928, LNT can be synthesized as described in WO 2012/155916 and WO 2013/044928, a mixture of LNT and LNnT can be made as described in WO 2013/091660, 2'-FL can be made as described in WO 2010/115934 and WO 2010/115935, 3-FL can be made as described in WO 2013/139344, 6'-SL and salts thereof can be made as described in WO 2010/100979, sialylated oligosaccharides can be made as described in WO 2012/113404 and mixtures of human milk oligosaccharides can be made as described in WO 2012/113405. As examples of enzymatic production, sialylated oligosaccharides can be made as described in WO 2012/007588, fucosylated oligosaccharides can be made as described in WO 2012/127410, and advantageously diversified blends of human milk oligosaccharides can be made as described in WO 2012/156897 and WO 2012/156898. With regard to biotechnological methods, WO 01/04341 and WO 2007/101862 describe how to make core human milk oligosaccharides optionally substituted by fucose or sialic acid using genetically modified E. coli.

In one embodiment, the synthetic composition can be in the form of a nutritional composition. For example, the nutritional composition can be a food composition, a rehydration solution, a medical food or food for special medical purposes, a nutritional supplement and the like. The nutritional composition can contain sources of protein, lipids and/or digestible carbohydrates and can be in powdered or liquid forms. The composition can be designed to be the sole source of nutrition or as a nutritional supplement.

Suitable protein sources include milk proteins, soy protein, rice protein, pea protein and oat protein, or mixtures thereof. Milk proteins can be in the form of milk protein concentrates, milk protein isolates, whey protein or casein, or mixtures of both. The protein can be whole protein or hydrolysed protein, either partially hydrolysed or extensively hydrolysed. Hydrolysed protein offers the advantage of easier digestion which can be important for humans with inflamed or compromised GI tracts. The protein can also be provided in the form of free amino acids. The protein can comprise about 5% to about 30% of the energy of the nutritional composition, normally about 10% to 20%.

The protein source can be a source of glutamine, threonine, cysteine, serine, proline, or a combination of these amino acids. The glutamine source can be a glutamine dipeptide and/or a glutamine enriched protein. Glutamine can be included due to the use of glutamine by enterocytes as an energy source. Threonine, serine and proline are important amino acids for the production of mucin. Mucin coats the GI tract and can improve mucosal healing. Cysteine is a major precursor of glutathione, which is key for the antioxidant defences of the body.

Suitable digestible carbohydrates include maltodextrin, hydrolysed or modified starch or corn starch, glucose polymers, corn syrup, corn syrup solids, high fructose corn syrup, rice-derived carbohydrates, pea-derived carbohydrates, potato-derived carbohydrates, tapioca, sucrose, glucose, fructose, sucrose, lactose, honey, sugar alcohols (e.g., maltitol, erythritol, sorbitol), or mixtures thereof. Preferably the composition is free from added lactose. Generally digestible carbohydrates provide about 35% to about 55% of the energy of the nutritional composition. A particularly suitable digestible carbohydrate is a low dextrose equivalent (DE) maltodextrin.

Suitable lipids include medium chain triglycerides (MCT) and long chain triglycerides (LCT). Preferably the lipid is a mixture of MCTs and LCTs. For example, MCTs can comprise about 30% to about 70% by weight of the lipids, more specifically about 50% to about 60% by weight. MCTs offer the advantage of easier digestion which can be important for humans with inflamed or compromised GI tracts. Generally, the lipids provide about 35% to about 50% of the energy of the nutritional composition. The lipids can contain essential fatty acids (omega-3 and omega-6 fatty acids). Preferably these polyunsaturated fatty acids provide less than about 30% of total energy of the lipid source.

Suitable sources of long chain triglycerides are rapeseed oil, sunflower seed oil, palm oil, soy oil, milk fat, corn oil, high oleic oils, and soy lecithin. Fractionated coconut oils are a suitable source of medium chain triglycerides. The lipid profile of the nutritional composition is preferably designed to have a polyunsaturated fatty acid omega-6 (n-6) to omega-3 (n-3) ratio of about 4:1 to about 10:1. For example, the n-6 to n-3 fatty acid ratio can be about 6:1 to about 9:1.

The nutritional composition may also include vitamins and minerals. If the nutritional composition is intended to be a sole source of nutrition, it preferably includes a complete vitamin and mineral profile. Examples of vitamins include vitamins A, B-complex (such as B1, B2, B6 and B12), C, D, E and K, niacin and acid vitamins such as pantothenic acid, folic acid and biotin. Examples of minerals include calcium, iron, zinc, magnesium, iodine, copper, phosphorus, manganese, potassium, chromium, molybdenum, selenium, nickel, tin, silicon, vanadium and boron.

The nutritional composition can also include a carotenoid such as lutein, lycopene, zeaxanthin, and beta-carotene. The total amount of carotenoid included can vary from about 0.001 μg/ml to about 10 μg/ml. Lutein can be included in an amount of from about 0.001 μg/ml to about 10 μg/ml, preferably from about 0.044 μg/ml to about 5 μg/ml of lutein. Lycopene can be included in an amount from about 0.001 μg/ml to about 10 μg/ml, preferably about 0.0185 μg/ml to about 5 μg/ml of lycopene. Beta-carotene can comprise from about 0.001 μg/ml to about 10 mg/ml, for example about 0.034 μg/ml to about 5 μg/ml of beta-carotene.

The nutritional composition preferably also contains reduced concentrations of sodium; for example, from about 300 mg/l to about 400 mg/l. The remaining electrolytes can be present in concentrations set to meet needs without providing an undue renal solute burden on kidney function. For example, potassium is preferably present in a range of about 1180 to about 1300 mg/l; and chloride is preferably present in a range of about 680 to about 800 mg/l.

The nutritional composition can also contain various other conventional ingredients such as preservatives, emulsifying agents, thickening agents, buffers, fibres and prebiotics (e.g. fructooligosaccharides, galactooligosaccharides), probiotics (e.g. B. animalis subsp. lactis BB-12, B. lactis HNO19, B. lactis Bi07, B. infantis ATCC 15697, L. rhamnosus GG, L. rhamnosus HNOOI, L. acidophilus LA-5, L. acidophilus NCFM, L. fermentum CECT5716, B. longum BB536, B. longum AH1205, B. longum AH1206, B. breve M-16V, L. reuteri ATCC 55730, L. reuteri ATCC PTA-6485, L. reuteri DSM 17938), antioxidant/anti-inflammatory compounds including tocopherols, carotenoids, ascorbate/vitamin C, ascorbyl palmitate, polyphenols, glutathione, and superoxide dismutase (melon), other bioactive factors (e.g. growth hormones, cytokines, TFG-β), colorants, flavours, and stabilisers, lubricants, and so forth.

The nutritional composition can be formulated as a soluble powder, a liquid concentrate, or a ready-to-use formulation. The composition can be fed to a human in need via a nasogastric tube or orally. Various flavours, fibres and other additives can also be present.

The nutritional compositions can be prepared by any commonly used manufacturing techniques for preparing nutritional compositions in solid or liquid form. For example, the composition can be prepared by combining various feed solutions. A protein-in-fat feed solution can be prepared by heating and mixing the lipid source and then adding an emulsifier (e.g. lecithin), fat soluble vitamins, and at least a portion of the protein source while heating and stirring. A carbohydrate feed solution is then prepared by adding minerals, trace and ultra-trace minerals, thickening or suspending agents to water while heating and stirring. The resulting solution is held for 10 minutes with continued heat and agitation before adding carbohydrates (e.g. the HMOs and digestible carbohydrate sources). The resulting feed solutions are then blended together while heating and agitating and the pH adjusted to 6.6-7.0, after which the composition is subjected to high-temperature short-time processing during which the composition is heat treated, emulsified and homogenized, and then allowed to cool. Water soluble vitamins and ascorbic acid are added, the pH is adjusted to the desired range if necessary, flavours are added, and water is added to achieve the desired total solid level.

For a liquid product, the resulting solution can then be aseptically packed to form an aseptically packaged nutritional composition. In this form, the nutritional composition can be in ready-to-feed or concentrated liquid form. Alternatively, the composition can be spray-dried and processed and packaged as a reconstitutable powder.

When the nutritional product is a ready-to-feed nutritional liquid, it may be preferred that the total concentration of HMOs in the liquid, by weight of the liquid, is from about 0.1% to about 1.5%, including from about 0.2% to about 1.0%, for example from about 0.3% to about 0.7%. When the nutritional product is a concentrated nutritional liquid, it may be preferred that the total concentration of HMOs in the liquid, by weight of the liquid, is from about 0.2% to about 3.0%, including from about 0.4% to about 2.0%, for example from about 0.6% to about 1.5%.

In another embodiment, the nutritional composition is in a unit dosage form. The unit dosage form can contain an acceptable food-grade carrier, e.g. phosphate buffered saline solution, mixtures of ethanol in water, water and emulsions such as an oil/water or water/oil emulsion, as well as various wetting agents or excipients. The unit dosage form can also contain other materials that do not produce an adverse, allergic or otherwise unwanted reaction when administered to a human. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

A unit dosage form of this invention can be administered orally, e.g. as a tablet, capsule, or pellet containing a predetermined amount of the mixture, or as a powder or granules containing a predetermined concentration of the mixture or a gel, paste, solution, suspension, emulsion, syrup, bolus, electuary, or slurry, in an aqueous or non-aqueous liquid, containing a predetermined concentration of the mixture. An orally administered composition can include one or more binders, inert diluents, flavouring agents, and humectants. An orally administered composition such as a tablet can optionally be coated and can be formulated to provide sustained, delayed or controlled release of the HMO.

A unit dosage form of this invention can also be administered by naso-gastric tube or direct infusion into the GI tract or stomach.

A unit dosage form of this invention can also include therapeutic agents such as antibiotics, probiotics, analgesics, and anti-inflammatory agents. The proper dosage of such a composition for a human can be determined in a conventional manner, based upon factors such as the human's condition, immune status, body weight and age. In some cases, the dosage will be at a concentration similar to that found for the HMOs of the composition in human breast milk. The required amount would generally be in the range from about 1 g to about 15 g per day, in certain embodiments from about 2 g to about 10 g per day, for example about 3 g to about 7 g per day. Appropriate dose regimes can be determined by methods known to those skilled in the art.

In further embodiment, the HMO can be comprised in a pharmaceutical composition. The pharmaceutical composition can contain a pharmaceutically acceptable carrier, e.g. phosphate buffered saline solution, mixtures of ethanol in water, water and emulsions such as an oil/water or water/oil emulsion, as well as various wetting agents or excipients. The pharmaceutical composition can also contain other materials that do not produce an adverse, allergic or otherwise unwanted reaction when administered to non-infants. The carriers and other materials can include solvents, dispersants, coatings, absorption promoting agents, controlled release agents, and one or more inert excipients, such as starches, polyols, granulating agents, microcrystalline cellulose, diluents, lubricants, binders, and disintegrating agents.

The pharmaceutical compositions can be administered orally, e.g. as a tablet, capsule, or pellet containing a predetermined amount, or as a powder or granules containing a predetermined concentration or a gel, paste, solution, suspension, emulsion, syrup, bolus, electuary, or slurry, in an aqueous or non-aqueous liquid, containing a predetermined concentration. Orally administered compositions can include binders, lubricants, inert diluents, flavouring agents, and humectants. Orally administered compositions such as tablets can optionally be coated and can be formulated to provide sustained, delayed or controlled release of the mixture therein.

The pharmaceutical compositions can also be administered by rectal suppository, aerosol tube, naso-gastric tube or direct infusion into the GI tract or stomach.

The pharmaceutical compositions can also include therapeutic agents such as antibiotics, probiotics, analgesics, and anti-inflammatory agents. The proper dosage of these compositions for a human can be determined in a conventional manner, based upon factors such condition, immune status, body weight and age. In some cases, the dosage will be at a concentration similar to that found for the HMOs in human breast milk. The required amount would generally be in the range from about 1 g to about 15 g per day, in certain embodiments from about 2 g to about 10 g per day, for example from about 3 g to about 7 g per day. Appropriate dose regimes can be determined by conventional methods.

For reducing fatigue in human, the amount of HMO(s) required to be administered will vary depending upon factors such as the risk and severity of the fatigue, any underlying medical condition or disease, age, the form of the composition, and other medications being administered. However, the required amount can be readily set by a medical practitioner and would generally be in the range from about 1 g to about 15 g per day, in certain embodiments from about 2 g to about 10 g per day, for example from about 3 g to about 7 g per day. An appropriate dose can be determined based on several factors, including, for example, body weight and/or condition, the severity of the fatigue being treated or prevented, other ailments and/or diseases, the incidence and/or severity of side effects and the manner of administration. Appropriate dose ranges may be determined by methods known to those skilled in the art. During an initial treatment phase, the dosing can be higher (for example 3 g to 15 g per day, preferably 3 g to 10 g per day). During a maintenance phase, the dosing can be reduced (for example, 1 g to 10 g per day, preferably 2 g to 7.5 g per day).

EXAMPLES

Example 1

A total of 163 male and female participants are recruited to participate in the study. The participants complete a baseline screening survey where they indicate any medical conditions, fatigue status, and various gastrointestinal and quality of life symptoms. For the symptoms, a 5-point Likert scale is used where a score of 1 means "No symptoms" and a score of 5 means "severe symptoms". Of the 163 participants, 84 indicate an elevated fatigue score. Further, the following underlying conditions are indicated:

| Condition | Number of participants |
| --- | --- |
| Irritable bowel syndrome | 36 |
| Diarrhoea | 42 |
| Constipation | 24 |
| Allergy | 46 |
| Food intolerance | 36 |
| Depression | 42 |
| Intestinal bowel disease | 12 |
| Coeliac disease | 4 |

Each participant is provided with an amount of HMO sufficient for 3 weeks of a daily dose of about 4 g of HMO. The HMO provided is either 2'-FL alone or a 4:1 mix of 2'-FL and LNnT (by weight).

After 3 weeks of intake, each participant completes a second survey where they indicate fatigue status, and various gastrointestinal and quality of life symptoms. The same 5-point Likert scale is used to assess the symptoms.

The process is repeated after 6 weeks, 9 weeks and 12 weeks.

Over the course to the 12 weeks, the participants indicate a 39% reduction in fatigue symptoms. Participants indicate increased focus and concentration.

Example 2

Twenty four male piglets (12 per treatment group) are treated from 48 h post-farrowing until 33 days of life with either control (Purina ProNurse Livestock Milk Replacer), or the intervention (control formula 1.5 g/l of 2'-FL and LNnT). Piglets are fed at a rate of 285 ml and 325 ml of reconstituted diet per kg body weight from day 2-6 and day 7-33, respectively. Piglets are euthanised on day 32 or 33 and hippocampal tissue is collected for analysis of mRNA expression.

Approximately 20 mg of hippocampal tissue are introduced in a Lysing Matrix D tube (MP Biomedicals, Santa Ana, Calif., USA), placed on ice, and 650 µL of lysis buffer (Agencourt RNAdvance Tissue Kit, Beckman Coulter, Indianapolis, Ind., USA) is added. Tubes are agitated for 2×1 minute at speed 6 on FastPrep®-24 (MP Biomedicals, Santa Ana, Calif., USA), and 400 µl of lysate are then extracted using the Agencourt RNAdvance Tissue Kit (Beckman Coulter, Indianapolis, Ind., USA) following the manufacturer's recommendations. RNA is quantified using the Quant-iT™ RiboGreen™ RNA Assay Kit (Invitrogen, Carlsbad, Calif., USA) on a Spectramax M2 (Molecular Devices, Sunnyvale, Calif., USA). RNA quality assessment is completed using a Fragment Analyzer 96 with Standard Sensitivity RNA Analysis Kit (15 nt) (Advanced Analytical Technologies, Inc., Ankeny, Iowa, USA). Relative mRNA copy number on 93 genes is quantified using the NanoString nCounter™ system (NanoString Technologies Inc., Seattle, Wash., USA) according to the manufacturer's instructions using 100 ng of RNA as the starting amount.

The intervention diet shows differential effects on gene expression compared to the control group. In particular intervention diet modulates expression of GABA type B receptor subunit 1 (GABBR1) and GABA Type A Receptor Beta2 Subunit (GABRB2).

The invention claimed is:

1. A method comprising:
    selecting a noninfant patient suffering from prolonged fatigue with an underlying medical condition of a food intolerance indicative of a need for dietary management;
    increasing a relative abundance of one or more adult-associated species of bifidobacteria selected from *Bifidobacterium adolescentis* phylogenetic group, Bifidobacteria *longum longum*, and *Bifidobacteria bifidum* in the gastrointestinal microbiota of the noninfant patient by administering an effective amount of one or more human milk oligosaccharides (HMOs), selected from the group consisting of 2'-fucosyllactose (2'-FL), 3-fucosyllactose (3-FL), difucosyllactose (DFL), lacto-N-tetraose (LNT), lacto-N-neotetraose (LNnT) and combinations thereof, to the noninfant patient for an initial treatment period of at least three weeks; and
    reducing severity and/or frequency of the prolonged fatigue experienced by the noninfant patient and associated with the underlying medical condition of the food intolerance.

2. The method of claim 1 in which the effective amount of the one or more HMOs administered to the noninfant patient is from about 3 g to about 7 g per day.

3. The method of claim 1, further comprising modulating a level of gamma-aminobutyric acid activity in the noninfant patient by administering the effective amount of the one or more HMOs.

4. The method of claim 1, wherein the one or more adult-associated species of bifidobacteria increased in relative abundance are *Bifidobacterium adolescentis*, and *Bifidobacterium longum longum*.

* * * * *